US008148333B2

(12) United States Patent
Dey et al.

(10) Patent No.: US 8,148,333 B2
(45) Date of Patent: Apr. 3, 2012

(54) STABLE COMPOSITION COMPRISING A PTHRP ANALOGUE

(75) Inventors: Michael J. Dey, Sandbach (GB);
Nathalie Mondoly, Le Chesnay (FR);
Benedicte Rigaud, Oulins (FR); Bart Henderson, Belmont, MA (US); C. Richard Lyttle, Bala Cynwyd, PA (US)

(73) Assignees: Radius Health, Inc., Cambridge, MA (US); Ipsen Pharma S.A.S., Boulogne-Billancourt (FR)

( * ) Notice: Subject to any disclaimer, the term of this patent is extended or adjusted under 35 U.S.C. 154(b) by 36 days.

(21) Appl. No.: 12/311,418

(22) PCT Filed: Oct. 3, 2007

(86) PCT No.: PCT/US2007/021216
§ 371 (c)(1),
(2), (4) Date: Sep. 24, 2009

(87) PCT Pub. No.: WO2008/063279
PCT Pub. Date: May 29, 2008

(65) Prior Publication Data
US 2010/0029556 A1    Feb. 4, 2010

Related U.S. Application Data

(60) Provisional application No. 60/848,960, filed on Oct. 3, 2006.

(51) Int. Cl.
*A61K 38/00* (2006.01)
*A61K 38/16* (2006.01)
*A61K 38/29* (2006.01)

(52) U.S. Cl. ............... 514/21.3; 514/16.7; 514/16.8; 514/16.9; 514/17.1

(58) Field of Classification Search .................. None
See application file for complete search history.

(56) References Cited

U.S. PATENT DOCUMENTS

| | | | |
|---|---|---|---|
| 5,589,452 A | 12/1996 | Krstenansky et al. |
| 5,693,616 A | 12/1997 | Krstenansky et al. |
| 5,695,955 A | 12/1997 | Krstenansky et al. |
| 5,723,577 A | 3/1998 | Dong |
| 5,798,225 A | 8/1998 | Krstenansky et al. |
| 5,807,823 A | 9/1998 | Krstenansky et al. |
| 5,821,225 A | 10/1998 | Vickery |
| 5,840,837 A | 11/1998 | Krstenansky et al. |
| 5,874,086 A | 2/1999 | Krstenansky et al. |
| 5,955,574 A | 9/1999 | Dong |
| 5,969,095 A | 10/1999 | Dong |
| 5,977,070 A | 11/1999 | Piazza et al. |
| 6,051,686 A | 4/2000 | Krstenansky et al. |
| 6,136,784 A | 10/2000 | L'Italien et al. |
| 6,544,949 B1 | 4/2003 | Dong |
| 6,583,114 B2 | 6/2003 | Vickery |
| 6,756,480 B2 | 6/2004 | Kostenuik et al. |
| 6,770,623 B1 | 8/2004 | Chang et al. |
| 6,849,710 B1 | 2/2005 | Arzeno |
| 6,921,750 B2 | 7/2005 | Dong |
| 7,371,721 B2 | 5/2008 | Henriksen et al. |
| 7,410,948 B2 | 8/2008 | Dong |
| 7,803,770 B2 | 9/2010 | Dey et al. |
| 2002/0077281 A1 | 6/2002 | Vickery |
| 2003/0039654 A1 | 2/2003 | Kostenuik et al. |
| 2003/0166836 A1 | 9/2003 | Dong |
| 2004/0214996 A1 | 10/2004 | Kostenuik et al. |
| 2005/0124537 A1 | 6/2005 | Kostenuik et al. |
| 2007/0299009 A1 | 12/2007 | Dong |
| 2008/0119401 A1 | 5/2008 | Dong |

FOREIGN PATENT DOCUMENTS

| | | |
|---|---|---|
| CA | 2555848 A1 | 8/2005 |
| CN | 1281370 A | 1/2001 |
| EP | 0 822 200 A1 | 2/1998 |
| EP | 0 822 200 B1 | 9/2004 |
| WO | WO 94/01460 | 1/1994 |
| WO | WO 96/40775 | 12/1996 |
| WO | WO 97/02834 | 1/1997 |
| WO | WO 97/07815 | 3/1997 |
| WO | WO 98/30590 | 7/1998 |
| WO | WO 99/12561 | 3/1999 |
| WO | WO 99/29337 A1 | 6/1999 |
| WO | WO 01/81415 A2 | 11/2001 |
| WO | WO 2004/060386 A1 | 7/2004 |
| WO | WO 2008/063279 A2 | 5/2008 |
| WO | WO2009/137093 A1 | 11/2009 |

OTHER PUBLICATIONS

Bellido, T. et al., "Estrogen Inhibit Apoptosis of Osteoblasts and Osteocytes through Rapid (Non-genomic) Activation of Extracellular Signal-Regulated Kinases (ERKs)," *Journal of Bone and Mineral Research*, 14(Supp 1)(Abstract SA135):S342 (1999).

Bodenner, D.L. et al., "Essential Requirement of the Estrogen Receptor α or β for (Non-Genomic) Anti-Apoptotic Effects of Estrogen," *Journal of Bone and Mineral Research*, 14(Supp 1)(Abstract F071):S227 (1999).

Fox, J., "Developments in Parathyroid Hormone and Related Peptides as Bone-Formation Agents," *Current Opinion in Pharmacology*, 2:338-344 (2002).

Gallagher, J.C. et al., "PTHrP(1-34) Analog, Sernparatide Acetate (RS-66271), Causes Sustained Increases in Spine in Postmanopausal Osteoporotic Women: Two Randomized Placebo-Controlled Trials," *Journal of Bone and Mineral Research*, 14(Supp 1 )(Abstract 1018):S137 (1999).

(Continued)

*Primary Examiner* — Elizabeth C Kemmerer
(74) *Attorney, Agent, or Firm* — Hamilton, Brook, Smith & Reynolds, P.C.

(57) ABSTRACT

The present invention provides a storage-stable composition containing a parathyroid hormone-related protein (PTHrP) analogue and methods of using a PTHrP analogue and the PTHrP compositions described herein to treat osteoporosis, to increase bone mass or to increase bone quality. The composition is storage stable, in sterile form, and in general may be stored at room temperature for at least several weeks to allow convenient parenteral administration to human patients.

13 Claims, 2 Drawing Sheets

OTHER PUBLICATIONS

Manolagas, S.C., "Activators of Non-Genomic Estrogen-Like Signalling (ANGELS): a Novel Class of Small Molecules with Bone Anabolic Properties," *Journal of Bone and Mineral Research*, 14(Supp 1)(Abstract 1191):S180 (1999).

Manolagas, S.C, et al., "Opposite Effects of Estrogen on the Life Span of Osteoblasts/Osteocytes Versus Osteoclasts In Vitro: An Explanation of the Imbalance between Formation and Resorption in Estrogen Deficiency," *Journal of Bone and Mineral Research*, 14(Supp 1)(Abstract 1147):S169 (1999).

Roe, E.B. et al., "Parathyroid Hormone 1-34 (hPTH 1-34) and Estrogen Produce Dramatic Bone Density Increases in Postmenopausal Osteoporosis—Results from a Placebo-Controlled Randomized Trial," *Journal of Bone and Mineral Research*, 14(Supp 1)(Abstract 1019):S137 (1999).

Sep. 25, 2008, International Search Report, PCT/US2007/021216.

Bostrom, M.P.G. et al., "Parathyroid Hormone-Related Protein Analog RS-66271 is an Effective Therapy for Impaired Bone Healing in Rabbits on Corticosteroid Therapy," *Bone*, 26(5): 2137-2412 (2000).

Culler, M.D. et al., "BIM-44058, a Novel Analog of PTHrP with Enhanced Bone Building Activity, but Decreased Calcium-Mobilization Potential," Twenty-Third Annual Meeting of the American Society of Bone and Mineral Research, Phoenix, Arizona, USA, Oct. 12-16, 2001, *J. Bone Miner. Res.*, (Abstract M460), 16(Suppl. 1):S540 (2001).

Culler, M.D. et al., "A Novel PTHRP Analog with Decreased Calcium-Mobilization Potential, but with Enhanced Bone Building Activity," S19, Abstract for the World Congress on Osteoporosis (Abstract P51SU), May 10-14, 2002, Lisbon.

Dempster, D.W. et al., "Anabolic Actions of Parathyroid Hormone on Bone," *Endocr Rev*, 14(6):690-709 (1993).

Dempster, D.W. et al., "Effects of Daily Treatment with Parathyroid Hormone on Bone Microarchitecture and Turnover in Patients with Osteoporosis: A Paired Biopsy Study," *J. Bone Miner Res.*, 16:1846-1853 (2001).

Dong, J.Z. et al., "Development of Highly Potent Human Parathyroid Hormone Analogs," *Peptides: Biology and Chemistry, Proceedings of the Chinese Peptide Symposium, 4th*, Chengdu, Peop. Rep. China, Jul. 21-25, 1996, pp. 173-175 (1998).

Dong, J.Z. et al., "Highly Potent Analogs of Human Parathyroid Hormone and Human Parathyroid Hormone-Related Protein," *Peptides: The Wave of the Future, Proceedings of the Second International and the Seventeenth American Peptide Symposium*, San Diego, CA USA, Jun. 9-14, 2001, pp. 668-669 (2001).

Dong, J.Z. et al., "Highly Potent Human Parathyroid Hormone Analogs," *Peptides: Frontiers of Peptide Science, Proceedings of the American Peptide Symposium, 15th*, Nashville, Jun. 14-19, 1997, pp. 541-542 (1999).

Everhart-Caye, M. et al., "Parathyroid Hormone (PTH)-Related Protein(1-36) is Equipotent to PTH(1-34) in Humans," *J. Clin Endocrinol Metab*, 81(1):199-208 (1996).

Fraher, L.J. et al., "A Comparison of the in Vivo Biochemical Responses to Exogenous Parathyroid Hormone-(1-34) [PTH-(1-34)] and PTH-Related Peptide-(1-34) in Man," *J Clin Endocrinol Metab*, 75(2):417-423 (1992).

Fraher, L.J. et al., "Comparison of the Pharmacokinetics of Parenteral Parathyroid Hormone-(1-34) [PTH-(1-34)] and PTH-Related Peptide-(1-34) in Healthy Young Humans," *J Clin Endocrinol Metal*, 80(1):60-64 (1995).

Frolik, C.A. et al., "Comparison of Recombinant Human PTH(1-34) (LY333334) with a C-Terminally Substituted Analog of Human PTH-Related Protein (1-34) (RS-66271): In Vitro Activity and In Vivo Pharmacological Effects in Rats," *J. Bone Miner. Res.*, 14(2):163-172 (1999).

Frolik, C.A. et al., "Reply: Further Data are Required to Assure that the Discrepant Binding Affinity is Explained by Different Receptor Conformations," *J. Bone Miner Res.*, 15(3):608 (2000).

Henry, J.G. et al., "Parathyroid Hormone-Related Protein-(1-36) is Biologically Active When Administered Subcutaneously to Humans," *J Clin Endocrinol Metab*, 82(3):900-906 (1997).

Hildebrand, T. et al., "Direct Three-Dimensional Morphometric Analysis of Human Cancellous Bone: Microstructural Data from Spine, Femur, Iliac Crest, and Calcaneus," *J. Bone Miner Res*, 14(7):1167-1174 (1999).

Hoare, S.R.J. and Usdin, T.B., "Letter to the Editor: The Discrepancy Between the Binding Affinity of PTH (1-34) and RS 66271 is Explained by Interaction of the PTH/PTHrP Receptor with G-Protein," *J. Bone Miner. Res.*, 15(3):605-607 (2000).

Hoare, S.R.J. and Usdin, T.B., "Quantitative Cell Membrane-Based Radioligand Binding Assays for Parathyroid Hormone Receptors," *J. Pharmacol. Toxicol.*, 41:83-90 (1999).

Horwitz, M.J. et al., "Continuous PTH and PTHrP Infusion Causes Suppression of Bone Formation and Discordant Effects on 1,25(OH)$_2$ Vitamin D," *J Bone Miner Res*, 20(10)1792-1803 (2005).

Horwitz, M.J. et al., "Direct Comparison of Sustained Infusion of Human Parathyroid Hormone-Related Protein-(1-36) [hPTHrP-(1-36)] Versus hPTH-(1-34) on Serum Calcium, Plasma 1,25-Dihydroxyvitamin D Concentrations, and Fractional Calcium Excretion in Healthy Human Volunteers," *J Clin Endocrinol Metab*, 88(4):1603-1609 (2003).

Horwitz, M.J. et al., "Safety and Tolerability of Subcutaneous PTHrP(1 -36) in Healthy Human Volunteers: a Dose Escalation Study," *Osteoporos Int*, 17:225-230 (2006).

Horwitz, M.J. et al., "Short-Term, High-Dose Parathyroid Hormone-Related Protein as a Skeletal Anabolic Agent for the Treatment of Postmenopausal Osteoporosis," *J Clin Endocrinol Metab*, 88(2):569-575 (2003).

Krstenansky, J.L. et al., "RS-66271: Molecular Design and in vivo Bone Anabolic Activity," Peptides 1994, Proceedings of the European Peptide Symposium, 23$^{rd}$, Braga, Port., Sep. 4-10, 1994:133-134 (1995).

Legrand, J. et al., "BIM-44058, a Novel PTHrP Analog, Does Not Increase Total Plasma Calcium in Cynomolgus Monkeys at an Effective Pharmacological Dose," Twenty-Third Annual Meeting of the American Society of Bone and Mineral Research, Phoenix, Arizona, USA, Oct. 12-16, 2001, *J Bone Miner Res* (Abstract M454) 16 (Suppl. 1):S539 (2001).

Legrand, J. et al., "BIM-44058, A Novel PTHrP Analog, Increases Bone Formation But Not Bone Resorption Histomorphometric Parameters in Old Ovariectomized Osteopenic Cynomolgus Monkeys," Twenty-Third Annual Meeting of the American Society of Bone and Mineral Research, Phoenix, Arizona, USA, Oct. 12-16, 2001, *J Bone Miner Res* (Abstract M455) 16 (Suppl. 1):S539 (2001).

Legrand, J. et al., "BIM-44058, a Novel PTHrP Analog, Restores in Vivo Spinal Bone Mineral Density in Old Ovariectomized Osteopenic Cynomolgus Monkeys," Twenty-Third Annual Meeting of the American Society of Bone and Mineral Research, Phoenix, Arizona, USA, Oct. 12-16, 2001, *J Bone Miner Res* (Abstract M453) 16 (Suppl. 1):S539 (2001).

Legrand, J-J. et al., "BIM-44058, A Novel PTHrP Analog, Restores BMD by Selectively Increasing Bone Formation in Old Ovariectomized, Osteopenic Cynomolgus Monkeys," S20, Abstract for the World Congress on Osteoporosis (Abstract P53SA), May 10-14, 2002, Lisbon.

Mannstadt, M. et al., "Receptors for PTH and PTHrP: Their Biological Importance and Functional Properties," *American Physiological Society: Invited Review*:F665-F675 (1999).

Martin, T.J., "Osteoblast-derived PTHrP is a Physiological Regulator of Bone Formation," *J Clin Invest*, 115(9):2322-2324 (2005).

Miao, D. et al., "Osteoblast-derived PTHrP is a Potent Endogenous Bone Anabolic Agent that Modifies the Therapeutic Efficacy of Administered PTH 1-34," *J Clin Invest*, 115(9):2402-2411 (2005).

Murrills, R.J. et al., "In vitro and in vivo Activities of C-Terminally Tuncated PTH Peptides Reveal a Disconnect Between cAMP Signaling and Functional Activity," *Bone*, 35:1263-1272 (2004).

Neer, R.M. et al., "Effect of Parathyroid Hormone (1-34) on Fractures and Bone Mineral Density in Postmenopausal Women with Osteoporosis," *N. Engl. J. Med.*, 344(19):1434-1441 (2001).

O'Dea, L.S., et al., "BA058, a Novel Analog of Human Parathyroid Hormone-Related Peptide (PTHrP), Induces Evidence of Bone Formation without Evidence of Bone Resorption over 7 Days of Exposure," *The Endocrine Society's 89$^{th}$ Annual Meeting* held on Jun. 2-5, 2007, (Abstract) P2-137:361 (published on May 11, 2007).

Odgaard, A. and Gundersen, H.J.G., "Quantification of Connectivity in Cancellous Bone, with Special Emphasis on 3-D Reconstructions," *Bone*, 14:173-182 (1993).

Odgaard, A., "Three-Dimensional Methods for Quantification of Cancellous Bone Arhitecture," *Bone*, 20(4):315-328 (1997).

Pellegrini, M. et al., "Addressing the Tertiary Structure of Human Parathyroid Hormone-(1-34)," *J. Biol. Chem.*, 273(17):10420-10427 (1998).

Pellegrini, M. et al., "RS-66271, a Clinical Candidate Derived from Parathyroid Hormone Related Protein: the Role of Enhanced Amphiphilic Helicity," Peptipes: Frontiers of Peptide Science, Proceedings of the American Peptide Symposium, 15$^{th}$, Nashville, Jun. 14-19, 1997 (1999), 392-393.

Pellegrini, M. et al., "Conformational Studies of RS-66271, an Analog of Parathyroid Hormone-Related Protein with Pronounced Bone Anabolic Activity," *J. Med. Chem.*, 40(19):3025-3031 (1997).

Plotkin, H. et al., "Dissociation of Bone Formation from Resorption during 2-Week Treatment with Human Parathyroid Hormone-Related Peptide-(1-36) in Humans: Potential as an Anabolic Therapy for Osteoporosis," *J Clin Endocrinol Metab*, 83(8):2786-2791 (1998).

Toniolo, C., "$C^\alpha, ^\alpha$-Symmetrically Disubstituted Glycines: Useful Building Blocks in the Design of Conformationally Restricted Peptides", *Janssen Chim. Acta*, 11:10-16 (1993).

Vickery, B.H. et al., "RS-66271, a C-Terminally Substituted Analog of Human Parathyroid Hormone-Related Protein (1-34), Increases Trabecular and Cortical Bone in Ovariectomized, Osteopenic Rats," *J. Bone Miner. Res.*, 11(12):1943-1951 (1996).

Notification Concerning Transmittal of International Preliminary Report on Patentability, and International Preliminary Report on Patentability, International Application No. PCT/US2007/021216, Date of Mailing Jun. 4, 2009.

Notification of Transmittal of the International Search Report and the Written Opinion of the International Searching Authority, or the Declaration, International Search Report, and Written Opinion of the International Searching Authority, International Application No. PCT/US2007/021216, Date of Mailing Sep. 25, 2008.

Notification of Transmittal of the International Search Report and the Written Opinion of the International Searching Authority, or the Declaration, International Search Report, and Written Opinion of the International Searching Authority, International Application No. PCT/US2009/002868, Date of Mailing Aug. 3, 2009.

Notification Concerning Transmittal of International Preliminary Report on Patentability, International Application No. PCT/US2009/002868, Date of Mailing Nov. 18, 2010.

English Translation of Chinese Office Action dated Oct. 12, 2010, Chinese Patent Application No. 200780037021.9.

U.S. Appl. No. 12/855,458, filed Aug. 12, 2010, by Dey et al.

Office Action, U.S. Appl. No. 12/151,975, Mail Date: Dec. 31, 2009.

Office Action, U.S. Appl. No. 12/151,975, Mail Date: May 18, 2010.

Notice of Allowance, U.S. Appl. No. 12/151,975, Date Mailed: Jul. 23, 2010.

Office Action, U.S. Appl. No. 12/855,458, Mail Date: Oct. 5, 2011.

```
                        SEQUENCE LISTING

<160> NUMBER OF SEQ ID NOS: 2

<210> SEQ ID NO 1
<211> LENGTH: 34
<212> TYPE: PRT
<213> ORGANISM: Homo Sapiens

<400> SEQUENCE: 1

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
             20                  25                  30

Thr Ala

<210> SEQ ID NO 2
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 29
<223> OTHER INFORMATION: Aib
```

-continued

```
<220> FEATURE:
<221> NAME/KEY: AMIDATION
<222> LOCATION: 34
<220> FEATURE:
<221> NAME/KEY: VARIANT
<222> LOCATION: 29
<223> OTHER INFORMATION: Xaa = Any Amino Acid

<400> SEQUENCE: 2

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Xaa Lys Leu His
             20                  25                  30

Thr Ala
```

STABLE COMPOSITION COMPRISING A PTHRP ANALOGUE

RELATED APPLICATION

This application is the U.S. National Stage of International Application No. PCT/US2007/021216, filed Oct. 3, 2007, published in English, and claims the benefit of U.S. Provisional Application No. 60/848,960, filed on Oct. 3, 2006. The entire teachings of the above application are incorporated herein by reference.

BACKGROUND OF THE INVENTION

Parathyroid hormone-related protein ("PTHrP") is a 139 to 173 amino acid-protein. PTHrP and certain analogs are known to be useful to improve bone mass and quality in the treatment of osteoporosis and related disorders. However, the commercial use of these proteins as pharmaceutical agents requires the development of a formulation that is acceptable in terms of storage stability and ease of preparation.

Furthermore, currently available osteoporosis drugs have limitations on suitable dosage ranges due to the unwanted side-effects, such as hypercalcemia and increased stimulation of bone resorption. These unwanted side-effects and resulting dose limitations reduce the beneficial effects which can be achieved from these drugs. Thus a need exists for compounds which can be administered at a dose which will increase the beneficial effects without an increase in the unwanted side-effects.

SUMMARY OF THE INVENTION

The present invention provides a storage-stable composition containing a parathyroid hormone-related protein (PTHrP) analogue and methods of using those analogues and compositions containing those analogues as described herein to treat osteoporosis, to increase bone mass or to increase bone quality. The composition is storage stable, in sterile form, and in general may be stored at room temperature for at least several weeks to allow convenient parenteral administration to human patients.

In one embodiment, the present invention provides a storage-stable composition suitable for administration to a subject (e.g., a human). The composition comprises a PTHrP analogue and an effective amount of buffer to maintain the pH of the composition between 2 and 7. In a particular embodiment, the PTHrP is [Glu$^{22,25}$, Leu$^{23,28,31}$, Aib$^{29}$, Lys$^{26,30}$]hPTHrP(1-34)NH$_2$ (SEQ ID NO.: 2).

In another embodiment, the present invention provides a sealed container containing a storage-stable composition suitable for administration to a subject. The composition comprises PTHrP or an analog thereof and an effective amount of buffer to maintain the pH of the composition between 2 and 7. In a particular embodiment, the PTHrP analogue is [Glu$^{22,25}$, Leu$^{23,28,31}$, Aib$^{29}$, Lys$^{26,30}$]hPTHrP(1-34)NH$_2$ (SEQ ID NO.: 2).

In another embodiment, the present invention provides a drug delivery device comprising one or more than one single-use container which comprises a storage stable composition comprising PTHrP or an analog thereof and an effective amount of buffer to maintain the pH of the composition between 2 and 7. In a particular embodiment, the PTHrP analogue is [Glu$^{22,25}$, Leu$^{23,28,31}$, Aib$^{29}$, Lys$^{26,30}$]hPTHrP(1-34)NH$_2$ (SEQ ID NO.:2).

In another embodiment, the present invention provides a drug delivery device comprising one or more than one multi-use container, which comprises a storage stable composition comprising PTHrP or an analog thereof and an effective amount of buffer to maintain the pH of the composition between 2 and 7. In a particular embodiment, the PTHrP analogue is [Glu$^{22,25}$, Leu$^{23,28,31}$, Aib$^{29}$, Lys$^{26,30}$]hPTHrP(1-34)NH$_2$ (SEQ ID NO.: 2).

In another embodiment the present invention provides a method of treating osteoporosis in a subject in need thereof comprising administering to the subject a single daily subcutaneous dose of [Glu$^{22,25}$, Leu$^{23,28,31}$, Aib$^{29}$, Lys$^{26,30}$]hPTHrP(1-34)NH$_2$ (SEQ ID NO.: 2) in an amount between 40 and 160 μg for a duration of time sufficient to treat the subject, typically between about 3 months to 36 months. In some embodiments, the treatment period is between about 3 months to 18 months.

In another embodiment the present invention provides a method of increasing bone mass or increasing bone quality in a subject in need thereof comprising administering to the subject a single daily subcutaneous dose of [Glu$^{22,25}$, Leu$^{23,28,31}$, Aib$^{29}$, Lys$^{26,30}$]hPTHrP(1-34)NH$_2$ (SEQ ID NO. 2) in an amount between 40 and 160 μg for a duration of time sufficient to treat the subject, typically between 3 months and 36 months. In some embodiments, the treatment period is between about 3 months to 18 months.

The PTHrP and analogue compositions of the invention exhibit storage stability in terms of hormone composition and activity. Furthermore, these compositions can be administered, in general, in higher dosages than currently available osteoporosis drugs, with the reduction or elimination of unwanted side-effects, such as, hypercalcemia or stimulation of bone resorption. This has the advantage of an increase in beneficial physiological effects due to the increased dosages and can result in a reduction in the length of treatment time.

DETAILED DESCRIPTION OF THE INVENTION

Figure 1:
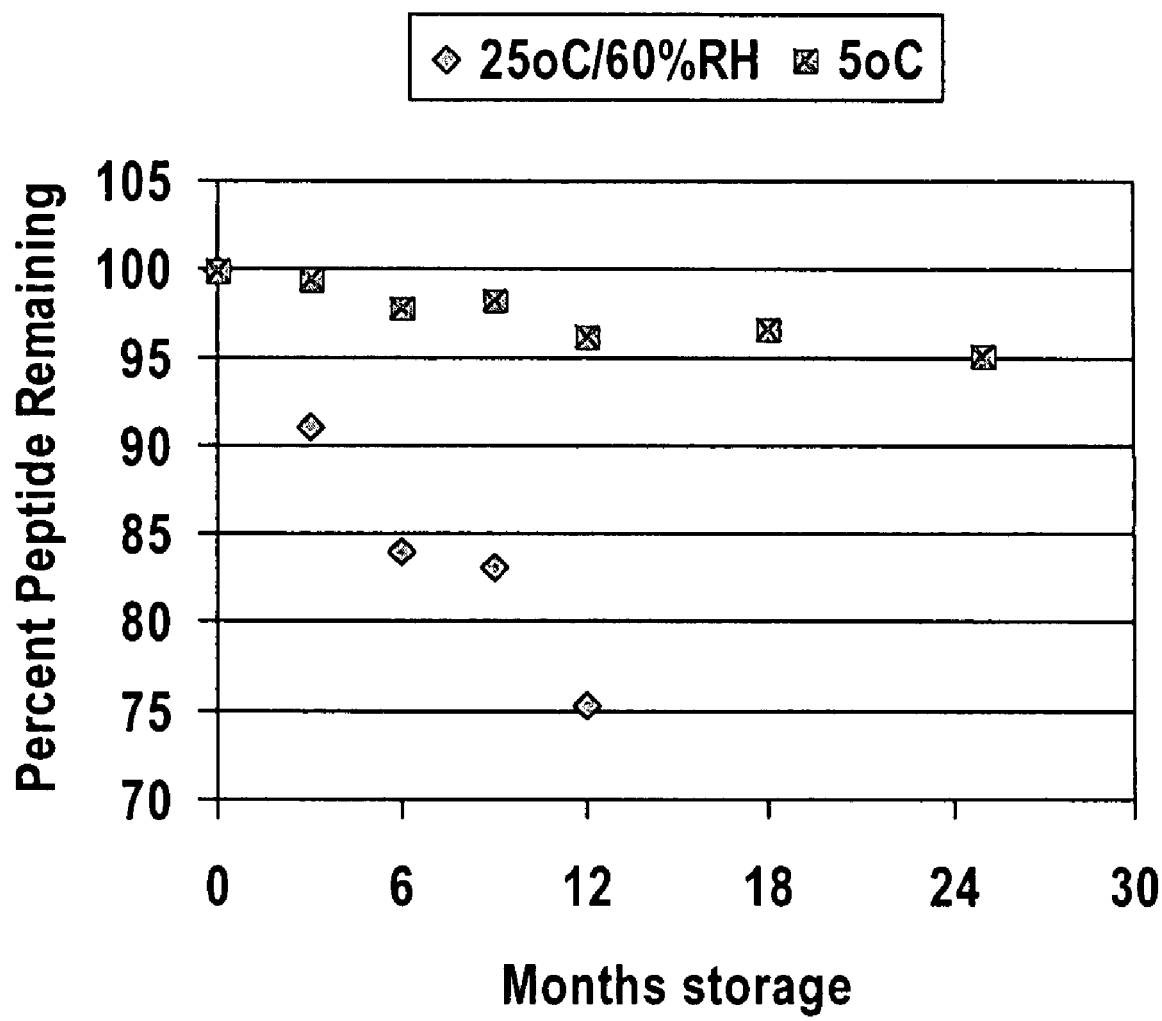
FIG. 1 is a graph showing the stability of SEQ ID NO. 2 over 24 months at 5° C. and 25° C. without any chemical stabilizer.

The sequence of native hPTHrP (1-34) is as follows:

Ala Val Ser Glu His Gln Leu Leu His Asp Lys Gly Lys Ser Ile Gln Asp Leu Arg Arg Arg Phe Phe Leu His His Leu Ile Ala Glu Ile His Thr Ala (SEQ ID NO: 1).

In a particular embodiment, the PTHrP analogue is [Glu$^{22,25}$, Leu$^{23,28,31}$, Aib$^{29}$, Lys$^{26,30}$]hPTHrP(1-34)NH$_2$ (SEQ ID NO.: 2).

Other PTHrP analogues are described in U.S. Pat. Nos. 6,921,750, 5,955,574, 6,544,949, 5,723,577, and 5,696,095 the entire contents of each of which are incorporated herein by reference.

A "buffer" as used herein is any acid or salt combination which is pharmaceutically acceptable and capable of maintaining the composition of the present invention within a desired pH range. Buffers in the disclosed compositions maintain the pH in a range of about 2 to about 7, about 3 to about 6, about 4 to about 6, about 4.5 to about 5.6, or about 5.1. Suitable buffers include, any pharmaceutical acceptable buffer capable of maintaining the above pH ranges, such as, for example, acetate, tartrate phosphate or citrate buffers. In one embodiment, the buffer is an acetate or tartrate buffer. In another embodiment the buffer is an acetate buffer. In one embodiment the buffer is acetic acid and sodium acetate.

In the disclosed compositions the concentration of buffer is typically in the range of about 0.1 mM to about 1000 mM, about 0.2 mM to about 200 mM, about 0.5 mM to about 50 mM, about 1 mM to about 10 mM or about 6 mM.

As used herein, an anti-microbial agent is a pharmaceutically acceptable preservative, suitable for administration to a subject, which inhibits, prevents or delays the growth or micro organisms including, for example bacteria, viruses and fungi in the compositions of the present invention. Suitable anti-microbial agents for use in the compositions and methods of the present invention include, but are not limited to, cresols, benzyl alcohol, phenol, benzalkonium chloride, benzethonium chloride, chlorobutanol, phenylethyl alcohol, methyl paraben, propyl paraben, thiomersal and phenylmercuric nitrate and acetate. In one embodiment the anti-microbial agents is m-cresol, chlorocresol or phenol. In another embodiment the anti-microbial agents is chlorocresol or phenol. In another embodiment the anti-microbial agents is phenol.

As used herein an effective amount of an anti-microbial agent is an amount effective to inhibits, prevents or delays the growth or micro organisms including, for example bacteria, viruses and fungi in the compositions of the present invention. In the compositions of the present invention, the amount of anti-microbial agent is typically in the range from about 0.1 to about 20 mg/ml, about 0.2 to about 30 mg/ml, about 0.2 to about 10 mg/ml, about 0.25 to about 5 mg/ml, about 0.5 to about 50 mg/ml, about 1 to about 10 mg/ml, about 3 mg/ml or about 5 mg/ml.

The compositions of the present invention typically are ready to administer, aqueous solutions which are sterile, storage-stable and pharmaceutically acceptable without the need for reconstitution prior to administration. The compositions of the present invention are suitable for administration to a subject which means that they are pharmaceutically acceptable, non-toxic, do not contain any components which would adversely affect the biological or hormonal effects of the peptide. The compositions of the present invention do not, for example, comprise any cells.

As used herein a composition of the present invention is storage-stable if the amount, purity of the PTHrP remains above about 95% of the original amount under one of the following conditions: (1) storage for over 2 years at 5° C.; or (2) storage for over 30 days at 25° C.

The compositions are typically stored in a sealed container, vial or cartridge which is typically suitable for long term storage. "Suitable for long-term storage" means that the vial, container or cartridge does not allow for the escape of components of the compositions of the present invention or the ingress of external components, such as, micro organisms when kept for at least 3 months at 25° C.

The compositions of the present invention are preferably administered by injection, typically subcutaneous injection.

The compositions of the present invention, can be stored in single-dose or multi-dose sealed containers, vials or cartridges. The sealed container, vial or cartridge is typically suitable for use with a single or multi-dose injection pen or drug delivery device, which typically allows the patient to administer the peptide themselves. The sealed container can comprise one or more doses of the peptide of the present invention, wherein each dose comprises an effective amount of the peptide as described herein.

A single-dose injection pen, or drug delivery device is typically a disposable device which uses a sealed container which comprises a single dose of an effective amount of a PTHrP in the compositions described herein. A multi-dose injection pen or drug delivery device typically contains more than one dose of an effective amount of a PTHrP thereof in the compositions described herein. The multi-dose pen can typically be adjusted to administer the desired volume of the storage stable compositions described herein. In certain embodiment the multi-dose injection pen prevents the ingress of microbial contaminants from entering the container or cartridge which can occur through multiple uses of one needle.

Injection pens, as used herein, can also comprise two containers one of which contains a PTHrP, as described herein, in a lyophilized powder, as described below, and the second container contains a liquid for reconstitution of the lyophilized powder. The contents of the two containers can be mixed prior to administration.

As discussed above the compositions of the present invention can be administered by injection. Suitable volumes of the compositions of the present invention for injection include about 0.5 to about 1 ml, about 0.1 to about 1 ml, about 0.02-to about 0.04 ml, about 0.1-to about 5.0 µl, or about 0.1-to about 1.0 µl.

In the compositions of the present invention the concentration of the peptides is from about 20 mg/ml to about 20,000 mg/ml, from about 100 mg/ml to about 10,000 mg/ml, from about 300 mg/ml to about 300 mg/ml, from about 500 mg/ml to about 2000 mg/ml and about 2 mg/ml.

The compositions of the present invention can also be lyophilized using lyophilization techniques known in the art and stored as a powder which can be reconstituted prior to administration. The term "lyophilization" as used herein is a freeze drying or dehydration technique which involves removing a solvent, preferably a water miscible solvent, more preferably water from a composition or the present invention, typically by sublimation under high vacuum when the composition is in a frozen state. Typically, lyophilization is carried out in lyophilization equipment (a lyophilizer), which comprises a drying chamber with variable temperature controls, a condenser to collect water, and a vacuum system to reduce the pressure in the drying chamber.

The terms "lyophilized composition", as used herein mean the solid residue or powder which is produced or which remains after the lyophilization procedure as defined above. The lyophilized composition of the present invention typically further comprise a pharmaceutically acceptable excipient. The term "pharmaceutically acceptable excipient" as used herein refers to a substance which is added to a solution prior to lyophilization to enhance characteristics such as the color, texture, strength, and volume of the lyophilized cake. Pharmaceutically acceptable excipients may be, for example, buffers and pH adjusters, crystalline bulking excipients, stabilizers, and tonicity raising agents.

In certain preferred embodiments the pharmaceutically acceptable excipient is a crystalline bulking excipient. The terms "crystalline bulking excipient" or "crystalline bulking agent" as used herein means an excipient which provides bulk and structure to the lyophilization cake. These crystalline bulking agents are inert and do not react with the peptide. In addition, the crystalline bulking agents are capable of crystallizing under lyophilization conditions.

Examples of suitable crystalline bulking agents include hydrophilic excipients, such as, water soluble polymers; sugars, such as mannitol, sorbitol, xylitol, glucitol, ducitol, inositiol, arabinitol, arabitol, galactitol, iditol, allitol, maltitol, fructose, sorbose, glucose, xylose, trehalose, allose, dextrose, altrose, lactose, glucose, fructose, gulose, idose, galactose, talose, ribose, arabinose, xylose, lyxose, sucrose, maltose, lactose, lactulose, fucose, rhamnose, melezitose, maltotriose, raffinose, altritol, their optically active forms (D-or L-forms) as well as the corresponding racemates; inorganic salts, both mineral and mineral organic, such as, calcium salts, such as the lactate, gluconate, glycerylphosphate, citrate, phosphate monobasic and dibasic, succinate, sulfate and tartrate, as well as the same salts of aluminum and magnesium; carbohydrates, such as, the conventional mono-and di-saccharides as well as the corresponding polyhydric alcohols; proteins, such as, albumin; amino acids, such as glycine; emulsifiable fats and polyvinylpyrrolidone. Preferred crystalline bulking agents are selected from the group consisting of glycine, mannitol, dextran, dextrose, lactose, sucrose, polyvinylpyrrolidone, trehalose, glucose and combinations thereof. Particularly useful bulking agents include dextran.

As used herein a stabilizer is a composition which maintains the chemical, biological or hormonal stability of the peptide. Examples of stabilizing agent include polyols which includes a saccharide, preferably a monosaccharide or disaccharide, e.g., glucose, trehalose, raffinose, or sucrose; a sugar alcohol such as, for example, mannitol, sorbitol or inositol, a polyhydric alcohol such as glycerine or propylene glycol or mixtures thereof and albumin.

The compositions described herein can be used to stimulate bone growth in a subject. Thus they are useful in the treatment of diseases or disorders associated with deficiency in bone growth such as osteoporosis and bone fractures. In one embodiment, the present invention is a method of treating osteoporosis in a subject comprising administering to the subject an effective amount of composition described herein.

As used herein, "treating" can include both prophylactic, and therapeutic treatment. For example, therapeutic treatment can include delaying inhibiting or preventing the progression of osteoporosis, the reduction or elimination of symptoms associated with osteoporosis. Prophylactic treatment can include preventing, inhibiting or delaying the onset of osteoporosis.

As used herein, an effective amount refers to an amount sufficient to elicit the desired response. In the present invention, the desired biological response is an decrease in the rate of bone loss and/or an increase in the bone mass or bone quality of a subject.

Suitable dosage for use in the compositions and methods of the present invention include from about 40 to about 160 µg, about 80 to about 120 µg about 80 to about 100 µg; or from about 40 to about 50 µg, about 50 to about 60 µg, about 60 to about 70 µg, about 70 to about 80 µg, about 80 to about 90 µg, about 90 to about 100 µg, about 100 to about 110 µg, about 110 to about 120 µg, about 120 to about 130 µg, about 130 to about 140 µg, about 140 to about 150 µg, about 150 to about 160 µg; or from 40 to about 45 µg, about 45 to about 50 µg, about 50 to about 55 µg, about 55 to about 60 µg, about 60 to about 65 µg, about 65 to about 70 µg, about 70 to about 75 µg, about 75 to about 80 µg, about 80 to about 85 µg, about 85 to about 90 µg, about 90 to about 95 µg, about 95 to about 100 µg, about 100 to about 105 µg, about 105 to about 110 µg, about 110 to about 115 µg, about 115 to about 120 µg, about 120 to about 125 µg, about 125 to about 130 µg, about 130 to about 135 µg, about 135 to about 140 µg, about 140 to about 145 µg, about 145 to about 150 µg, about 150 to about 155 µg, about 155 to about 160 µg administered once per day, once every other day, twice per week once per week, once every two weeks, once per month. The doses can be a pulsatile injection, for example, once per month which causes pulsatile release of singles doses of the composition described herein.

When the dosages described above are administered once per day, once per week etc., typically the dosages are of equal amounts.

The subject as used herein can be an animal, for example, a mammal, such as a human.

A pharmaceutically acceptable salt is a salt which is suitable for administration to a subject, such as, a human. The peptides of the present invention can have one or more sufficiently acidic proton that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like. The peptides of the present invention having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

The compositions of the present invention typically do not show any or show reduced side-effects such as hypercalcemia and typically do not increase the stimulation of bone resorption at the dosage listed above. This reduction in side effects allows for administration of higher doses than commercially available osteoporosis drugs.

The compositions of the present invention can be administered by injection as described herein.

The compositions of the present invention may be administered alone or in combination with an additional therapeutic agent, such as an antiresorptive therapy, for example, bisphonsphonates and calcitonin.

EXEMPLIFICATION

Example 1

Demonstrates [Glu$^{22,25}$, Leu$^{23,28,31}$, Aib$^{29}$, Lys$^{26,30}$]hPTHrP(1-34)NH$_2$ (SEQ ID NO.: 2) Stability at Low Acetate Concentration (1 mM), Without Stabilizer

TABLE 1

| Material | Supplier | Unitary Formula (per cartridge) |
|---|---|---|
| (SEQ ID NO.: 2) | Ipsen Ireland | 0.140 mg (free base) |
| Tri-hydrate sodium acetate 0.1 N | Prolabo | 14.6 mg |
| Acetic acid 0.1 N | Prolabo | 1.9 mg qs pH 5.1 |
| Water for Injection | Meram | qs 1.4 g |
| Type I clear glass Cartridge 1.5 ml, washed, siliconised and sterilised | Bünderglass via Vetter | 1 |
| Grey PTFE bromobutyl cartridge rubber stopper | Daikyo | 1 |
| Chlorobutyl rubber-metal cartridge crimp | West Pharmaceutical | 1 | qs = quantity sufficient to achieve

The formulation delivered 100 mcg of (SEQ ID NO.: 2) per 0.1 ml. (SEQ ID NO.: 2) was dissolved in Water for Injection containing dilute acetate buffer to give pH 5.1 was used.

Results confirm excellent chemical stability over 24 months, at 5° C. as shown in FIG. 1. This solution contains no stabilizer or preservative and only 6 mM acetate buffer.

In summation for (SEQ ID NO.: 2), stabilizer is not needed to give good stability in solution.

Example 2

Use of Citric Acid Buffer in Lyophilized Form of (SEQ. ID NO.: 2)

TABLE 2

| Material | Supplier | Unitary Formula (per vial) |
|---|---|---|
| (SEQ ID NO.: 2) | Ipsen Ireland | 0.1 mg (free base) |
| Dextran 70 | Interchemical | 50 mg |
| Citric acid 0.25% (w/v) | Prolabo | qs pH 4.5* |
| Water for injections** | Meram | qs 1 g |
| Type I clear glass vial, 11-13 ml | Verretubex | 1 |
| Grey chlorobutyl PTFE stopper, 20 mm | Daikyo | 1 |
| Flip-off metal crimp | West Pharma | 1 |

**to get pH 5-5.5 after lyophilisation removed after freeze-drying step.

The solutions in TABLE 2 were reconstituted with NaCl 0.9%, to give:

ONE vial of 2 ml (=50 μg/ml) providing 10 to 80 μg/d doses (with injections of 200 μl to 1.6 ml), or ONE vial of 5 ml (=20 μg/ml solution) providing 5 to 40 μg/d doses (with injections of 250 μl-2 ml).

Citric acid was used to adjust pH and Dextran was used to provide a bulking agent to aid cake formation during lyophilization.

Figure 2:
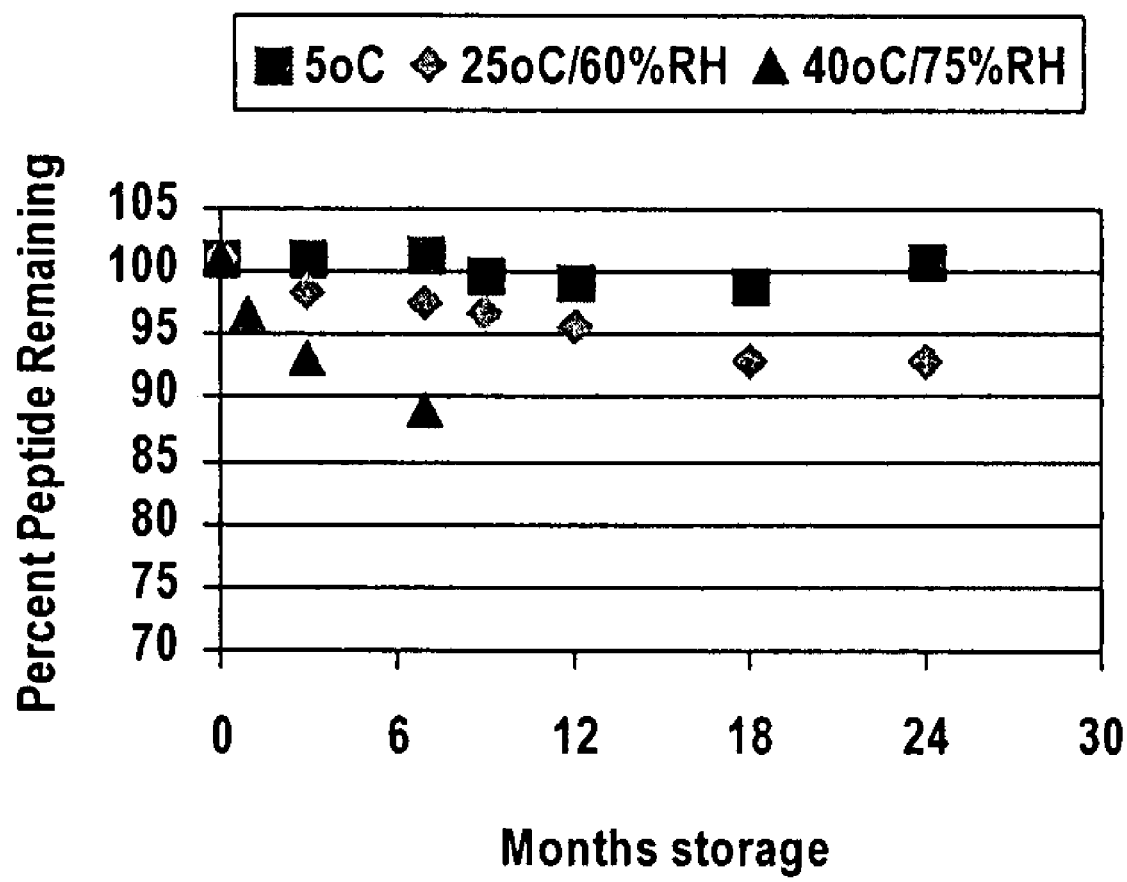
FIG. 2 is a graph showing the stability of lyophilized SEQ ID NO. 2 over 24 months at 5° C. 25° C. and 40° C.

The solutions described were lyophilized in glass vials, and stored at various temperatures for up to 24 months. The content of [Glu$^{22,25}$, Leu$^{23,28,31}$, Aib$^{29}$, Lys$^{26,30}$]hPTHrP(1-34)NH$_2$ (SEQ ID NO.: 2), purity and physical tests were conducted on samples removed from storage at different times. Results are presented in FIG. 2, for peptide concentration, as percent remaining. The data in FIG. 2 shows excellent stability over 24 months at 2-8° C.

Example 3

Screening of Formulations for [Glu$^{22,25}$, Leu$^{23,28,31}$, Aib$^{29}$, Lys$^{26,30}$]hPTHrP(1-34)NH$_2$ (SEQ ID NO.: 2) to Compare Different Preservatives TABLE 3 below shows Methyparaben and Benzyl Alcohol are not suitable preservatives for use with [Glu$^{22,25}$, Leu$^{23,28,31}$, Aib$^{29}$, Lys$^{26,30}$]hPTHrP(1-34)NH$_2$ (SEQ ID NO.: 2), as precipitation and/or inactivity in preservative activity was seen.

TABLE 3

| | Example 3a | Example 3b | Example 3c | Example 3d | Example 3e |
|---|---|---|---|---|---|
| Methylparaben | 1.5 mg/mL | 1.35 mg/mL | — | — | — |
| Propylparaben | — | 0.15 mg/mL | — | — | — |
| Phenol | — | — | 5 mg/mL | — | — |
| Chlorocresol | — | — | — | 3 mg/mL | — |
| Benzyl alcohol | — | — | — | — | 10 mg/mL |
| Preservative effectiveness test | Failed | Pass | Pass | Pass | Pass |
| Observationo or Issues | Precipitation observed | — | — | — | — |
| Preservative effectiveness test after storage 4.5 months at 5° C. | Not Tested as precipitated initially | Pass | Pass | Pass | Fail |

Solutions were prepared containing [Glu$^{22,25}$, Leu$^{23,28,31}$, Aib29, Lys$^{26,31}$]hPTHrP(1-34)NH$_2$ (SEQ ID NO.: 2) 2 mg/ml, acetate buffer 6 mM and water for injection, with various different preservatives added at concentrations recommended for effective antimicrobial activity. Solutions were prepared at room temperature, by dissolution of the various ingredients in water for injection, with stirring over <30 minutes to ensure complete dissolution, Solutions were filtered through 0.2 micron filter and filled into glass vials, to which a rubber stopper was applied and crimped in place to ensure complete closure.

The solution with methylparaben was less acceptable due to precipitation and inactivity immediately after manufacture of the solution. The solutions were then stored for up to 3 months at 25° C., and up to 4.5 months at 5° C. and the preservative effectiveness test repeated. as described in Example 5.

Example 4

Evaluation of Anti-Microbial Preservative Effectiveness of Various Concentrations of [Glu$^{22,25}$, Leu$^{23,28,31}$, Aib$^{29}$, Lys$^{26,30}$]hPTHrP(1-34)NH$_2$ (SEQ ID NO.: 2) Compositions (Stability Study)

TABLE 4

|  | P87228 | P87229 | P87230 | P87231 |
|---|---|---|---|---|
| (SEQ ID NO.: 2) | 2 mg/mL | 2 mg/mL | 2 mg/mL | 2 mg/mL |
| Anti-microbial | Phenol 5 mg/mL | Chlorocresol 3 mg/mL | Chlorocresol 2 mg/mL | Benzyl alcohol 10 mg/mL |
| Acetate buffer | pH 5.1 | pH 5.1 | pH 5.1 | pH 5.1 |

The solutions were tested according to European Pharmacopoeia, Chapter 5.1.3 "Efficacité de la conservation anti-microbienne" (Anti-microbial effectiveness test) to prove the effectiveness of the preservative.

TABLE 5

Preservative effectiveness test after manufacturing

| Organisms: Bacteria | Initial organism concentration in cfu/mL | Test interval | Nb of cfu present/preparation (plate-count method) | | | |
|---|---|---|---|---|---|---|
| | | | P87228 Phenol 5 mg/ml | P87229 Chlorocresol 3 mg/ml | P87230 Chlorocresol 2 mg/ml | P87231 Benzyl alc. 10 mg/ml |
| Staphylococcus aureus | 3.8 × 10$^5$ | T 0 | 3.4 × 10$^5$ | <5 | <5 | 4.7 × 10$^5$ |
| | | T + 6 hrs | <5 | <5 | <5 | 6.8 × 10$^2$ |
| | | T + 24 hrs | <5 | <5 | <5 | <5 |
| | | T + 28 days | 5 (*) | <5 | <5 | <5 |
| Pseudomonas aeruginosa | 1.3 × 10$^6$ | T 0 | 5 | <5 | <5 | 1.5 × 10$^2$ |
| | | T + 6 hrs | <5 | <5 | <5 | <5 |
| | | T + 24 hrs | <5 | <5 | <5 | <5 |
| | | T + 28 days | <5 | <5 | <5 | <5 |
| E. coli | 6.7 × 10$^5$ | T 0 | 7.2 × 10$^3$ | <5 | <5 | 1.1 × 10$^5$ |
| | | T + 6 hrs | <5 | <5 | <5 | <5 |
| | | T + 24 hrs | <5 | <5 | <5 | <5 |
| | | T + 28 days | <5 | <5 | <5 | <5 |

| Organism: Yeast and mold | Initial organism concentration in cfu/mL | Test interval | Nb of cfu present/preparation (plate-count method) | | | |
|---|---|---|---|---|---|---|
| | | | P87228 Phenol 5 mg/ml | P87229 chlorocresol 3 mg/ml | P87230 chlorocresol 2 mg/ml | P87231 Benzyl alc. 10 mg/ml |
| Aspergillus niger | 3.4 × 10$^5$ | T 0 | 4.0 × 10$^5$ | <5 | <5 | 4.1 × 10$^5$ |
| | | T + 7 days | <5 | <5 | <5 | <5 |
| | | T + 28 days | <5 | <5 | <5 | <5 |
| Candida albicans | 3.9 × 10$^5$ | T 0 | 4.4 × 10$^5$ | <5 | <5 | 3.8 × 10$^5$ |
| | | T + 7 days | <5 | <5 | <5 | 5 |
| | | T + 28 days | <5 | <5 | <5 | <5 |
| Results: | Conform | — | Conform | Conform | Conform | Conform |

Preservative effectiveness test results after 3 months storage at 25° C.

| Organisms: Bacteria | Initial organism concentration in cfu/mL | Test interval (days) | Nb of cfu present/preparation (plate-count method) | | | |
|---|---|---|---|---|---|---|
| | | | P87228 Phenol 5 mg/ml | P87229 chlorocresol 3 mg/ml | P87230 chlorocresol 2 mg/ml | P87231 Benzyl alc. 10 mg/ml |
| Staphylococcus aureus | 2.7 × 10$^5$ (P87228, P87229, P87231) 5.2 × 10$^5$ (P87230) | 0 hr | 1.9 × 10$^5$ | <5 | <5 | 3.8 × 10$^5$ |
| | | 6 hr | 30 | <5 | <5 | 5.9 × 10$^3$ |
| | | 24 hr | <5 | <5 | <5 | <5 |
| | | 28 day | <5 | <5 | <5 | <5 |

TABLE 5-continued

| | | | | | | |
|---|---|---|---|---|---|---|
| *Pseudomonas aeruginosa* | $9.9 \times 10^5$ (P87228, P87229, P87231) $8.5 \times 10^5$ (P87230) | 0 hr 6 hr 24 hr 28 day | <5 <5 <5 <5 | <5 <5 <5 <5 | <5 <5 <5 <5 | <5 <5 <5 <5 |
| *E. coli* | $6.8 \times 10^5$ (P87228, P87229, P87231) $9.5 \times 10^5$ (P87230) | 0 hr 6 hr 24 hr 28 day | $1.7 \times 10^5$ <5 <5 <5 | <5 <5 <5 <5 | <5 <5 <5 <5 | $8.0 \times 10^4$ 5 <5 <5 |

| | Initial | | Nb of cfu present/preparation (plate-count method) | | | |
|---|---|---|---|---|---|---|
| Organism: Yeast and mold | organism concentration in cfu/mL | Test interval | P87228 Phenol 5 mg/ml | P87229 Chlorocresol 3 mg/ml | P87230 Chlorocresol 2 mg/ml | P87231 Benzyl alc. 10 mg/ml |
| *Aspergillus niger* | $3.3 \times 10^5$ (P87228, P87229, P87231) $4.1 \times 10^5$ (P87230) | 0 hr 7 day 28 day | $3.8 \times 10^5$ <5 <5 | 55 <5 <5 | 70 <5 <5 | $4.1 \times 10^5$ <5 <5 |
| *Candida albicans* | $2.7 \times 10^5$ (P87228, P87229, P87231) $3.7 \times 10^5$ (P87230) | 0 hr 7 day 28 day | $4.0 \times 10^5$ <5 <5 | <5 <5 <5 | <5 <5 <5 | $3.8 \times 10^5$ <5 <5 |
| Results: | Conform | — | Conform | Conform | Conform | Not Conform |

Preservative effectiveness test results after 4.5 months storage at 5° C.

| | Initial | | Nb of cfu present/preparation (plate-count method) | | | |
|---|---|---|---|---|---|---|
| Organisms: Bacteria | organism concentration in cfu/mL | Test interval (days) | P87228 Phenol 5 mg/ml | P87229 chlorocresol 3 mg/ml | P87230 chlorocresol 2 mg/ml | P87231 Benzyl alc. 10 mg/ml |
| *Staphylococcus aureus* | $5.4 \times 10^5$ | 0 hr 6 hr 24 hr 28 day | $4.1 \times 10^5$ <5 <5 <5 | <5 <5 <5 <5 | <5 <5 <5 <5 | $5.1 \times 10^5$ $7.2 \times 10^3$ <5 <5 |
| *Pseudomonas aeruginosa* | $9.7 \times 10^5$ | 0 hr 6 hr 24 hr 28 day | <5 <5 <5 <5 | <5 <5 <5 <5 | <5 <5 <5 <5 | <5 <5 <5 <5 |
| *E. coli* | $6.1 \times 10^5$ | 0 hr 6 hr 24 hr 28 day | $7.0 \times 10^4$ <5 <5 <5 | 5 <5 <5 <5 | 5 <5 <5 <5 | $4.2 \times 10^4$ <5 <5 <5 |

| | Initial | | Nb of cfu present/preparation (plate-count method) | | | |
|---|---|---|---|---|---|---|
| Organism: Yeast and mold | organism concentration in cfu/mL | Test interval | P87228 Phenol 5 mg/ml | P87229 Chlorocresol 3 mg/ml | P87230 Chlorocresol 2 mg/ml | P87231 Benzyl alc. 10 mg/ml |
| *Aspergillus niger* | $5.3 \times 10^5$ | 0 hr 7 day 28 day | $3.7 \times 10^5$ <5 <5 | $1.8 \times 10^3$ <5 <5 | $7.5 \times 10^3$ <5 <5 | $4.1 \times 10^5$ <5 <5 |
| *Candida albicans* | $4.1 \times 10^5$ | 0 hr 7 day 28 day | $4.5 \times 10^5$ <5 <5 | <5 <5 <5 | 5 <5 <5 | $4.5 \times 10^5$ <5 <5 |
| Results: | Conform | — | Conform | Conform | Conform | Not Conform |

(*) *Bacillus* Gram +, different from *St. Aureus* –> result conform

Nb of cfu = number of colony forming units

TABLE 5 shows Phenol, Chlorocresol and Benzyl Alcohol all produce compliant results immediately after manufacture for both Bacteria and Yeasts/moulds. After 3 and 4.5 months storage, the preservative efficacy is maintained for Phenol and Chlorocresol, for both Bacteria and Yeasts/moulds. However, for Benzyl Alcohol, the efficacy against Bacteria is not compliant, as the data shows insufficient rate of kill against *S. Aureus* (TABLE 5).

Example 5

Chemical Stability of Different Formulations

TABLE 6 details the chemical stability of the formulations described in Example 4.

TABLE 6

[Glu$^{22, 25}$, Leu$^{23, 28, 31}$, Aib$^{29}$, Lys$^{26, 30}$]hPTHrP(1-34)NH$_2$
(SEQ ID NO.: 2) stability results

| | | Storage conditions: 25° C., 60% RH (SEQ ID NO.: 2) content in mg/mL (% initial concentration at t = 0) | | |
|---|---|---|---|---|
| Batch | Composition | 0 month | 1 month | 3 months |
| P87228 | (SEQ ID NO.: 2) (2 mg/ml)/Phenol (5 mg/ml) | 1.90 (100%) | 1.88 (98.9%) | 1.83 (96.3%) |
| P87229 | (SEQ ID NO.: 2) (2 mg/ml)/Chlorocresol (3 mg/ml) | 1.98 (100%) | 1.96 (99.0%) | 1.94 (98.0%) |
| P87231 | (SEQ ID NO.: 2) (2 mg/ml)/Benzyl Alcohol (10 mg/ml) | 1.93 (100%) | 1.89 (97.9%) | 1.86 (96.4%) |

| | | Storage conditions: 5° C. (SEQ ID NO.: 2) content in mg/mL (% initial concentration at t = 0) | | |
|---|---|---|---|---|
| Batch | Composition | 0 month | 3 month | 4.5 month |
| P87228 | (SEQ ID NO.: 2) (2 mg/ml)/Phenol (5 mg/ml) | 1.90 (100%) | 1.91 (100.5%) | 1.89 (99.5%) |
| P87229 | (SEQ ID NO.: 2) (2 mg/ml)/Chlorocresol (3 mg/ml) | 1.98 (100%) | 1.96 (99.0%) | 1.97 (99.5%) |
| P87231 | (SEQ ID NO.: 2) (2 mg/ml)/Benzyl Alcohol (10 mg/ml) | 1.93 (100%) | 1.94 (100.5%) | 1.92 (99.5%) |

As can be seen from TABLE 6 and [Glu$^{22,25}$, Leu$^{23,28,31}$, Aib$^{29}$, Lys$^{26,30}$]hPTHrP(1-34)NH$_2$ (SEQ ID NO.: 2) solution stability is not significantly influenced by the preservative selected. TABLE 7 details the content of each preservative for the same formulations.

TABLE 7

Preservative stability results

| | | Storage conditions: 25° C., 60% RH Preservative content in mg/ml (% initial concentration at t = 0) | | |
|---|---|---|---|---|
| Batch | Composition | 0 month | 1 month | 3 month |
| P87228 | (SEQ ID NO.: 2) (2 mg/ml)/Phenol (5 mg/ml) | 4.86 (100%) | 4.82 (99.2%) | 4.79 (98.6%) |
| P87229 | (SEQ ID NO.: 2) (2 mg/ml)/Chlorocresol (3 mg/ml) | 2.78 (100%) | 2.70 (97.1%) | 2.56 (92.1%) |
| P87231 | (SEQ ID NO.: 2) (2 mg/ml)/Benzyl Alcohol (10 mg/ml) | 9.92 (100%) | 9.83 (99.1%) | 9.82 (99.0%) |

| | | Storage conditions: 5° C. Preservative content in mg/mL (% initial concentration at t = 0) | | |
|---|---|---|---|---|
| Batch | Composition | 0 month | 3 month | 4.5 month |
| P87228 | (SEQ ID NO.: 2) (2 mg/ml)/Phenol (5 mg/ml) | 4.86 (100%) | 4.83 (99.4%) | 4.84 (99.6%) |
| P87229 | (SEQ ID NO.: 2) (2 mg/ml)/Chlorocresol (3 mg/ml) | 2.78 (100%) | 2.73 (98.2%) | 2.74 (98.6%) |
| P87231 | (SEQ ID NO.: 2) (2 mg/ml)/Benzyl Alcohol (10 mg/ml) | 9.92 (100%) | 9.89 (99.7%) | 9.94 (100.2%) |

As can be seen from TABLE 7 chlorocresol is the preservative which has the lower stability, with greater loss in preservative content under both 5 and 25° C. storage.

While this invention has been particularly shown and described with references to example embodiments thereof, it will be understood by those skilled in the art that various changes in form and details may be made therein without departing from the scope of the invention encompassed by the appended claims.

What is claimed is:

1. A storage-stable composition suitable for administration to a subject comprising:
   a) a PTHrP analogue having the sequence [$Glu^{22,25}$, $Leu^{23,28,31}$, $Aib^{29}$, $Lys^{26,30}$] $hPTHrP(1-34)NH_2$ (SEQ ID NO.2); and
   b) an effective amount of a pH buffer to maintain the pH in a range of about 4.5 to about 5.6.

2. The storage-stable composition according to claim 1, wherein said pH is about 5.1.

3. The storage stable composition according to claim 1, wherein said pH buffer is selected from the group consisting of acetate, tartrate, phosphate and citrate buffers.

4. The storage-stable composition according to claim 3, wherein said pH buffer is an acetate buffer.

5. The storage-stable composition according to claim 4, wherein said acetate buffer is acetic acid and sodium acetate.

6. The storage-stable composition according to claim 5, wherein said buffer is present in a concentration range of about 1 mM to about 10 mM.

7. The storage stable composition according to claim 6, wherein said buffer is present in a concentration of about 6 mM.

8. The storage-stable composition according to claim 1, further comprising an effective amount of an anti-microbial agent.

9. The storage-stable composition according to claim 8, wherein said anti-microbial agent is phenol.

10. The storage-stable composition according to claim 9, wherein said phenol is present in a concentration from about 0.25 to about 5 mg/mL.

11. The storage-stable composition according to claim 10, wherein said phenol is present in a concentration of about 5 mg/mL.

12. The storage-stable composition according to claim 1, wherein said PTHrP analogue is present in a concentration of about 2 mg/mL.

13. The storage-stable composition according to claim 1, wherein said composition does not contain a chemical stabilizer.

* * * * *